(12) United States Patent
Degala et al.

(10) Patent No.: US 9,511,156 B2
(45) Date of Patent: *Dec. 6, 2016

(54) SYSTEMS, METHODS, AND DEVICES FOR STERILIZING ANTISEPTIC SOLUTIONS

(71) Applicant: CAREFUSION 2200, INC., San Diego, CA (US)

(72) Inventors: Satish Degala, Arlington Heights, IL (US); Christopher Matthew McGinley, Highland Park, IL (US); Kenneth Bruce Thurmond, Deer Park, IL (US)

(73) Assignee: Carefusion 2200, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/788,333

(22) Filed: Jun. 30, 2015

(65) Prior Publication Data

US 2015/0297764 A1 Oct. 22, 2015

Related U.S. Application Data

(63) Continuation-in-part of application No. 14/198,457, filed on Mar. 5, 2014, now Pat. No. 9,078,934, which is a continuation of application No. 14/150,488, filed on Jan. 8, 2014.

(51) Int. Cl.
*A61L 2/00* (2006.01)
*A61L 2/04* (2006.01)
(Continued)

(52) U.S. Cl.
CPC ............. *A61L 2/04* (2013.01); *A01N 43/40* (2013.01); *A01N 47/44* (2013.01); *A61L 2/28* (2013.01)

(58) Field of Classification Search
CPC .................................................. A61L 2/0023
USPC .............................................................. 422/28
See application file for complete search history.

(56) References Cited

U.S. PATENT DOCUMENTS

| 4,106,654 A | 8/1978 | Jones |
| 4,438,011 A | 3/1984 | Howes |

(Continued)

FOREIGN PATENT DOCUMENTS

| CN | 102993056 A | 3/2013 |
| CN | 103202827 A | 7/2013 |

OTHER PUBLICATIONS

Dictionary.com definition of bottle; http://dictionary.reference.com/browse/bottle; accessed Apr. 30, 2015.

(Continued)

*Primary Examiner* — Kevin Joyner
(74) *Attorney, Agent, or Firm* — Arent Fox LLP (57) ABSTRACT

A method for sterilizing an antiseptic solution includes providing a plurality of containers containing the antiseptic solution, the antiseptic solution having an initial purity, selecting a sterilization temperature from about 85° C. to about 135° C. and an sterilization time from about 1 minute to about 19 hours, heating the antiseptic solution in the plurality of containers to the selected sterilization temperature, maintaining the temperature for the selected sterilization time, and terminating the heating of the antiseptic solution when the sterilization time expires. After terminating the heating, the antiseptic solution in the plurality of containers has a post-sterilization purity. The sterilization temperature and the sterilization time are selected such that after terminating the heating, the antiseptic solution is sterile and have a post-sterilization purity of at least about 92% and the percentage point change in purity from the initial purity to the post-sterilization purity is at most about 5%.

29 Claims, 2 Drawing Sheets

(51) Int. Cl.
*A01N 47/44* (2006.01)
*A61L 2/28* (2006.01)
*A01N 43/40* (2006.01)

(56) References Cited

U.S. PATENT DOCUMENTS

| | | | |
|---|---|---|---|
| 4,646,629 | A | 3/1987 | Creed et al. |
| 7,868,016 | B2 | 1/2011 | Singh et al. |
| 8,062,649 | B2 | 11/2011 | Asmus et al. |
| 8,110,144 | B2 | 2/2012 | Morales |
| 8,383,038 | B2 | 2/2013 | Kitano |
| 2007/0178051 | A1 | 8/2007 | Pruitt et al. |
| 2008/0139519 | A1 | 6/2008 | Ashley et al. |
| 2013/0094995 | A1 | 4/2013 | Koyama |
| 2014/0322072 | A1 | 10/2014 | Margoosian et al. |
| 2015/0217008 | A1* | 8/2015 | Zwingenberger ......... A61L 2/07 134/25.1 |

OTHER PUBLICATIONS

International Search Report dated Apr. 13, 2015 issued in International Patent Application No. PCT/US15/10465.

Small, H. et al., "Efficacy of adding 2 percent (w/v) chlorhexidine gluconate to 70 percent (v/v) isopropyl alcohol for skin disinfection prior to peripheral venous cannulation", Infection Control and Hospital Epidemiology, vol. 29, pp. 963-965; abstract; title (2008).

* cited by examiner

SYSTEMS, METHODS, AND DEVICES FOR STERILIZING ANTISEPTIC SOLUTIONS

This application is a Continuation-In-Part of U.S. application Ser. No. 14/198,457, filed Mar. 5, 2014, now U.S. Pat. No. 9,078,934, which is a Continuation of U.S. application Ser. No. 14/150,488, filed Jan. 8, 2014, the disclosure of the prior applications is hereby incorporated in their entirety by reference.

FIELD OF THE INVENTION

Aspects of the present invention relate to the field of sterilization, and in particular, to sterilization of topical antiseptic solutions.

BACKGROUND OF THE INVENTION

In the United States there are currently no regulations regarding the sterilization requirements of topical antiseptic solutions. Therefore, antiseptic solutions currently sold in the United States generally do not undergo a sterilization process. In other jurisdictions, however, such as European Union (EU) countries, some degree of sterilization is required. A known antiseptic solution containing 2% w/v chlorhexidine gluconate in 70% v/v isopropanol in water, manufactured by CareFusion Corp., is sterilized for EU countries using a known sterilization method.

The known method of sterilization involves heat treating glass ampoules containing the chlorhexidine gluconate solution in a convection oven at 76-80° C. for 24-31 hours. It is currently believed that relatively low temperature and relatively long processing time is necessary to sufficiently sterilize the solution without overly degrading the antimicrobial molecules, thereby avoiding reducing the concentration and purity of the chlorhexidine gluconate contained therein as an antiseptic. Degrading the antimicrobial molecules creates undesired impurities as well as lowers the overall concentration of the active drug moiety. Regulations in the United States and EU countries limit the amount of impurities that may be present in the antiseptic solution. Furthermore, a convection oven, which utilizes air to conduct heat, is an inefficient process because the initial heating of the solution from room temperature (also referred herein as "ramp up" time) and eventual cooling down of the solution back to room temperature (also referred herein as "cool down" time) is relatively long. For example the ramp up time for the solution to reach the sterilization temperature can be 2-6 hours while the cool down period can be 1-2 hours. Accordingly, the time that the chlorhexidine gluconate solution is exposed to the sterilizing temperature (i.e., the time at 76-80° C.) in the known method can be 22 to 24 hours, while the total processing time (i.e., including ramp up, sterilization and cool down time) may be around 25 to 32 hours.

It is the industry belief that high temperature sterilization is not suitable due to the expected degradation. See, for example, Kelly M. Pyrek, "Sterility of Antiseptic Products: FDA Investigates, Deliberates on Potential Recommendations," *Infection Control Today* (July 2013): 24-26 and Block, Seymour S. *Disinfection, Sterilization, and Preservation*. Philadelphia: Lippincott Williams & Wilkens, 322-323. 2001.

Thus, there is an unmet need in the art for a method of sterilizing antiseptic solutions that has a shorter, more efficient processing time, and provides a sterile solution while maintaining sufficient purity of the antiseptic solution to comply with regulatory requirements.

SUMMARY OF THE INVENTION

Aspects of the present invention overcome the above identified problems, as well as others, by providing systems, methods, and devices for efficiently sterilizing antimicrobial solutions while maintaining antimicrobial efficacy as an antiseptic and purity of the active drug moiety to comply with regulatory requirements.

In one example aspect the method for sterilizing an antiseptic solution comprises providing a plurality of containers containing the antiseptic solution, the antiseptic solution having an initial purity; selecting a sterilization temperature from about 85° C. to about 135° C. and a sterilization time from about 1 minute to about 19 hours; heating the antiseptic solution in the plurality of containers to the selected sterilization temperature; maintaining the antiseptic solution in the plurality of containers at the selected sterilization temperature for the selected sterilization time; and terminating the heating of the antiseptic solution in the plurality of containers when the selected sterilization time expires. After terminating the heating, the antiseptic solution in the plurality of containers has a post-sterilization purity. The sterilization temperature and the sterilization time are selected such that after terminating the heating, the antiseptic solution in the plurality of containers is sterile and has a post-sterilization purity of at least about 92% and the percentage point change in purity from the initial purity to the post-sterilization purity is at most about 5%.

In another aspect, the sterilization temperature and sterilization time may be selected such that the selected sterilization time and selected sterilization temperature satisfy the following relationship:

$85° C. \leq y < 125° C.$, a)

$y \geq -6.14 \cdot \ln x + 123.2$ for $1 \leq x \leq 552$, and $y \leq -10.38 \cdot \ln x + 156.9$ for $21.5 \leq x \leq 1123$; or $125° C. \leq y \leq 135° C.$, b)

$x \geq 1$ and $y \leq -10.38 \sim \ln x + 156.9$ for $9.1 \leq x \leq 21.5$, wherein y is the sterilization temperature and x is the sterilization time in minutes.

In another example aspect, the sterilization temperature and the sterilization time are selected such that after terminating the heating, the antiseptic solution in the plurality of containers has a post-sterilization purity of at least about 94% and the percentage point change in purity from the initial purity to the post-sterilization purity is at most about 4%.

In another example aspect, the antiseptic solution in the plurality of containers comprises about 70% v/v isopropanol in water and about 2.0% w/v chlorhexidine gluconate.

In an another example aspect, the sterilization temperature is about 95° C. and the sterilization time is from about 90 minutes to about 6.5 hours. In another aspect, the sterilization temperature is about 110° C. and the sterilization time is from about 6 minutes to about 90 minutes. In another aspect the sterilization temperature is about 120° C. and the sterilization time is from about 2 minutes to about 35 minutes.

In another example aspect, the selected sterilization temperature and the selected sterilization time are chosen such that after terminating the heating, the antiseptic solution in the plurality of containers has a post-sterilization purity of at least about 96% and the percentage point change in purity from the initial purity to the post-sterilization purity is at most about 3%.

In another example aspect, the selected sterilization temperature and the selected sterilization time are chosen such that after terminating the heating, the antiseptic solution in the plurality of containers has a post-sterilization purity of at least about 98% and the percentage point change in purity from the initial purity to the post-sterilization purity is at most about 2%.

Additional advantages and novel features relating to aspects of the present invention will be set forth in part in the description that follows, and in part will become more apparent to those skilled in the art upon examination of the following or upon learning by practice thereof.

DETAILED DESCRIPTION

Aspects of the present invention overcome the above identified problems, as well as others, by providing systems, methods, and devices for sterilizing an antiseptic solution while maintaining antimicrobial efficacy and while complying with regulatory requirements.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of sterilization methods disclosed herein.

The term "about" as used herein preferably means±5% and more preferably ±1% of the provided value.

Aspects of the present invention include a method of sterilizing antiseptic solution contained in a container. The method may include heating antiseptic solution contained within a container or ampoule to a certain temperature and maintaining the temperature for a certain amount of time sufficient to sterilize the solution while maintaining sufficient purity of the antiseptic solution to comply with regulatory requirements. The antimicrobial efficacy directly relates to the purity of the antiseptic solution. Generally, when the purity of the antiseptic molecules is too low, the solution is not as effective as an antimicrobial solution. Furthermore, higher levels of impurities within an antiseptic solution can have a deleterious impact on patient health.

The container is preferably a self-contained structure, formed of a material suitable for containing the antiseptic solution. In an aspect, the container may be made of a frangible material such that upon application of sufficient force the container fractures. For example, the material may comprise plastic or glass. The terms "container" and "ampoule" are used interchangeably herein. The wall of the container may have a thickness sufficient to withstand the sterilization process, transport, and storage. When the container is frangible, the material and thickness may also be sufficient to allow the container to be fractured upon the application of localized pressure. The thickness range may vary depending on the container size. Example thicknesses for glass or plastic containers include from about 0.15 mm to about 0.45 mm. In another example aspect, the container may comprise a non-frangible material, such as a metal such as a pouch comprising or consisting of a polymeric and/or foil material, steel, aluminum, etc., capable of withstanding the sterilization process. For example, the container may be a retort-like foil pouch having a composite material of polymeric and foil. An example thickness of the pouch may be about 0.002 inches to 0.010 inches.

While antiseptic solutions are of particular focus herein, the container may alternatively contain medicaments, chemical compositions, cleansing agents, cosmetics, or the like. For example, the container may be filled with antiseptic compositions (e.g., compositions comprising one or more antiseptic molecules), preferably an antimicrobial liquid or gel composition. For example, the antiseptic solution may contain non-active ingredients with functions that include moisturizing, skin smoothing, visualization, solubility, stability, viscosity, wetting, etc.

The antiseptic solution may comprise an alcoholic solvent. For example, the alcoholic solvent may be selected from the group consisting of ethanol, isopropanol, and n-propanol. The amount of solvent may be from about 40% v/v to about 90% v/v, more preferably about 50% v/v to about 80% v/v, and still more preferably about 65% v/v to about 80% v/v. The remaining volume of the solution may be water or another solvent. For example the solution may contain from about 10% v/v to about 60% v/v, more preferably about 20% to about 50% v/v, and still more preferably about 20% to about 35% v/v water.

The container may contain antiseptic solution of a sufficient amount, sufficient concentration, and sufficient purity to be applied to a desired surface and have an antimicrobial effect on the desired surface. In one aspect, the desired surface is a patient's skin. It will be appreciated that the amount of antiseptic solution may vary. In one aspect the amount of antiseptic solution may be 0.01-100 mL of antiseptic. More preferably, the amount of antiseptic solution needed may be about 0.5-60 mL and still preferably may be about 0.5-30 mL. Examples include 0.67, 1, 1.5, 3, 10.5, 25, and 26 mL of antiseptic. In a situation where a larger amount of solution is desired, e.g., 26 mL, multiple smaller containers may be implemented in a single applicator (e.g., two 13 mL containers).

Suitable antiseptic molecules include bis-(dihydropyridinyl)-decane derivatives (e.g. octenidine salts) and/or biguanides (e.g., chlorhexidine salts). As used herein, the term "derivative" refers to a) a chemical substance that is related structurally to a first chemical substance and derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. Examples of biguanides/biguanide derivatives other than chlorhexidine/chlorhexidine salts include alexidine, alexidine salts, polyhexamide, polyhexamide salts, polyaminopropyl biguanide, polyaminopropyl biguanide salts, and other alkyl biguanides. Preferred antiseptic agents include octenidine salts, such as octenidine dihydrochloride (a bis- (dihydropyridinyl)-decane derivative and a cationic surfactant), and chlorhexidine salts, such as chlorhexidine gluconate (a cationic biguanide). The concentration of the antiseptic may vary depending on the specific antiseptic species used or the desired antimicrobial effect that is desired. For example, when using octenidine or an octenidine salt the concentration may vary from about 0.0001% w/v to about 2.0% w/v, more preferably from about 0.01% w/v to about 0.5% w/v, and still more preferably from about 0.1% w/v to about 0.4% w/v. When chlorhexidine or a chlorhexidine salt is used, the concentration may be from about 0.1% w/v to about 2.5% w/v, more preferably from about 0.5% w/v to about 2.25% w/v, and still more preferably about 1.2% w/v to about 2.0% w/v.

In an aspect, when chlorhexidine or a chlorhexidine salt is used, the purity of the solution, when applied to the skin (e.g., after the sterilization method described herein), may be at least about 92% pure, more preferably at least about 94% pure, still more preferably at least about 96% pure, and still more preferably at least about 98% pure. As used herein, purity means the percent concentration of antiseptic molecules in solution relative to the total concentration of antiseptic molecules plus concentration of substances that are derived from or related to the antiseptic molecule. For example, a 95% pure antiseptic solution means that if there are 100 molecules that are either antiseptic molecules or molecules derived from or related to the antiseptic molecule, 95 of the molecules are the antiseptic molecule and 5 of those molecules are derived from or related to the antiseptic molecule. These molecules derived from or relating to the antiseptic molecule have reduced or no antimicrobial activity. Thus, a lower purity solution will have lower antimicrobial efficacy as fewer of the target antiseptic molecules are delivered to the patient's skin. Further, a lower purity solution will not comply with regulatory requirements. By measuring the concentration of antiseptic molecules in solution as compared to concentration of antiseptic molecules and molecules derived from or related to the antiseptic molecule, one can determine the purity of the solution and whether the purity is sufficient to comply with regulatory requirements.

In a preferred aspect, the antiseptic solution provided in the container comprises about 70% v/v alcohol solvent in water and about 2.0% w/v antiseptic molecules. In a preferred aspect the solvent may be isopropanol and the antiseptic molecule may be chlorhexidine gluconate.

It has been found that when the antiseptic solution within the container is brought to a particular temperature and maintained at that temperature for a particular amount of time, the solution is sufficiently sterilized while maintaining sufficient antimicrobial efficacy as an antiseptic and while satisfying regulatory requirements. In an aspect of the present invention, the antiseptic solution may be brought to a temperature (also referred to herein as the "sterilization temperature") from about 85° C. to about 135° C., more preferably about 90° C. to about 125° C., and still more preferably about 95° C. to about 120° C.

As used herein, the term "sterilization time" means the length of time at which the solution is at the sterilization temperature. That is, the "sterilization time" does not include the time it takes for a solution to reach the sterilization temperature (i.e., does not include "ramp up" time) and also does not include the time it takes for the solution to return to the temperature the solution was at prior to the heating (i.e., does not include "cool down" time). The time it takes for the temperature of the solution to reach the sterilization temperature is referred herein as the "ramp up" time and the time to return to the starting temperature is referred herein as the "cool down" time. As used herein, the term "sterilization temperature" means the temperature or temperature range that the solution reaches and maintains during the sterilization time, independent of the starting temperature of the solution. For purposes of illustration only, a sterilization time of 90 minutes and a sterilization temperature of 95° C. for a solution starting at 21° C. would mean that the period of time starting from the moment the solution reaches 95° C. and ending the moment the solution falls below 95° C. during the beginning of the cool down process is 90 minutes. Thus, the time it takes from the solution to rise from 21° C. to 95° C. (i.e., ramp-up time) and the time it takes for the solution to return to 21° C. (i.e., cool-down time) is not included in the sterilization time.

The predetermined sterilization time and sterilization temperature provided herein generally assume the thermal exposure during the ramp-up and the cool-down does not contribute to the sterilization of the drug product as on a small scale these processes can be considered instantaneous. However, on a commercial scale, the time spent heating the product up will contribute to the overall lethality of the sterilization process, allowing the steady-state sterilization time to be decreased. When the ramp-up and cool-down contributions to the cycle are applied, the sterilization of the drug product can be described by the F-value calculated for each predetermined sterilization time and sterilization temperature using the following equation (see "Laboratory Manual for Food Canners and Processors", Vol. 1, AVI Publishing Co., Westport, Conn., 1968):

$$F = \Delta t \sum 10^{\frac{T-T_s}{z}}$$

where:
T is the temperature of the sterilized product at a particular time t.
$\Delta t$ is the time interval between subsequent measurements of T.
Ts=the target sterilization temperature
z=a temperature coefficient, normally assumed to be equal to 10° C., but calculable for specific microorganisms and therefore a variable For the purposes for illustration only, a sterilization temperature of 121° C. with a predetermined sterilization time of 6 minutes (i.e. ramp-up and cool-down do not contribute to the sterilization of the drug product) corresponds to a minimum F-value of 6 minutes at 121° C. ($F_{121}$) in order to sterilize the drug product. This minimum required F-value can be used to quantify a process in which the ramp-up and cool-down do contribute to the sterilization of the drug product. In such a process, the contribution for the ramp-up and cool-down on the minimum required F-value can be calculated. If during a sterilization cycle defined by an $F_{121}$=6 minutes a temperature of 121° C. is not reached, the cycle parameters could still be met per the calculation of $F_{121}$ as a summation of thermal input during the actual cycle.

In an aspect, the sterilization time may be no more than about 19 hours, more preferably no more than about 13 hours, more preferably no more than about 5 hours, more preferably no more than about 3 hours, more preferably no more than 2 hours, more preferably no more than 1 hour, more preferably no more than 40 minutes, more preferably no more than about 25 minutes, more preferably no more than 6 minutes, and more preferably no more than 1 minute.

It has been found that combinations of sterilization temperature and sterilization time can be selected to provide a sterilized antiseptic solution having sufficient purity to comply with regulatory requirements when used as an antiseptic. For example, for a sterilization temperature of about 85° C., the sterilization time may be at least about 9 hours to about 19 hours. For a sterilization temperature of about 95° C., the sterilization time may be at least about 1.5 hours and up to about 6.5 hours. For a sterilization temperature of about 105° C., the sterilization time may be at least about 17 minutes to about 2.5 hours. For a sterilization temperature of about 110° C., the sterilization time may be at least about 6 minutes and up to about 90 minutes. For a sterilization temperature of about 115° C., the sterilization time may be from about 3 minutes to about 55 minutes. For a sterilization temperature of about 120° C., the sterilization time may be at least about 2 minutes and up to about 35 minutes. For a sterilization temperature of about 125° C., the sterilization time may be from about 1 minute to about 22 minutes. For a sterilization temperature of about 130° C., the sterilization time may be at least about 1 minute and up to 14 minutes. For a sterilization temperature of about 135° C., the sterilization time may be from about 1 minute to about 9 minutes. In an aspect of the present invention, the above example sterilization temperatures and sterilization times may be applied to an antiseptic solution comprising about 70% v/v isopropanol and about 2.0% w/v chlorhexidine gluconate or other antiseptic solutions described above.

It has been found that heating the antiseptic solution contained in the container to the above sterilization temperatures and maintaining the temperature for the above sterilization times, sufficiently sterilizes the solution, while maintaining sufficient purity to comply with regulatory requirements. The amount of degradation of the antiseptic molecule can be quantified by measuring the initial purity of antiseptic solution prior to the ramp up time (i.e., prior to the process of bringing the solution up to the sterilization temperature) and measuring the post-sterilized purity of antiseptic solution after the cool down time (i.e., after the antiseptic solution returns to the temperature the solution was at prior to the process of bringing the solution up to the sterilization temperature). Thus, as used herein, the "initial purity" is the purity prior to ramp up and "post-sterilization purity" is the purity of the solution after cool down. In an aspect of the present invention, the initial purity of the antiseptic solution, e.g., chlorhexidine gluconate, may be at least about 94%, preferably at least about 97%, and more preferably at least about 98%. The meaning of purity is provided above. The resulting post-sterilized solution is found to have sufficient purity to provide the desired antimicrobial efficacy as an antiseptic and to comply with regulatory requirements.

In an example aspect, it has been found that chlorhexidine gluconate molecules degrade into one or more the following molecules when heat treated: N-[[6-[[[(4-chlorophenyl)carbamimidoyl]carbamimidoyl]-amino]hexyl]carbamimidoyl]urea, N-(4-chlorophenyl)guanidine, N-(4-chlorophenyl) urea, 1-(6-aminohexyl)-5-(4-chlorophenyl) biguanide, N-(4-chlorophenyl)-N'-[[6-[[[(4-chlorophenyl)carbamimidoyl]carbamimidoyl]amino]hexyl]carbamimidoyl]urea, 1-(4-chlorophenyl)-5-[6-[[(phenylcarbamimidoyl)carbamimidoyl]amino]hexyl]biguanide, 1-[6-(carbamimidoylamino)hexyl]-5-(4-chlorophenyl)-biguanide, and 4-chloroaniline. Thus, in an example aspect, the purity of the solution can be determined by comparing the amount of chlorhexidine to all of the above-listed chlorhexidine gluconate related substances. However, it should be noted that the above list is not exhaustive. One having ordinary skill in the art would be able to determine which molecules are degradants of the antiseptic molecule after the sterilization process.

As noted above, the purity of the antiseptic solution after the heating has been terminated and when the solution has returned to the temperature the solution was at prior to the process of bringing the solution up to the sterilization temperature (for example ambient temperature) is referred herein as the post-sterilization purity. As noted above, the post-sterilization purity is preferably measured when the antiseptic solution has cooled because degradation may occur during cooling. In an aspect of the present invention, by selecting an appropriate combination of sterilization temperature and sterilization time, the post-sterilization purity may be maintained relatively close to the initial purity, while still being sterile. In particular, the combination of sterilization temperature and sterilization time are chosen such that the percentage point change in purity from the initial purity to the post-sterilization purity is at most about 5%, more preferably at most about 4%, more preferably at most about 3%, and most preferably at most about 2%. It should be understood that the percentage point change refers to the absolute percentage point difference between the initial purity and the post-sterilization purity. For example, a change in initial purity of 95% to a post-sterilization purity of 90% is a percentage point change of 5%.

In addition to maintaining a sufficient purity, it has been found that the proper combination of sterilization temperature and sterilization time can be selected such that the solution is sterile. As used herein, sterile means "7 day sterility" as tested following the procedures described in U.S. Pharmacopeial Convention (USP) Chapter 55 "Biological Indicators—Resistance Performance Tests," USP 36; Official from May 1, 2013. Sterile also means completely free of microbes, immediately following sterilization. In an aspect, Geobacillus stearothermophilus may be used as a test microbe. Thus, in an aspect, a sterile solution would have no growth of Geobacillus stearothermophilus shown by the '7 day sterility' testing described above. In another aspect, a solution inoculated with Geobacillus stearothermophilus would be completely free of viable Geobacillus stearothermophilus immediately following the sterilization method.

In another aspect of the present invention, it was found that the inventive method has a sterility assurance level (SAL) of at least about $10^{-6}$ under particular combination of sterilization temperature and sterilization time. SAL is a measurement of probability of a microorganism occurring on an item following a sterilization procedure. A SAL of $10^{-6}$ means there is a 1 in 1,000,000 chance of a viable microorganism occurring in a sterilized product. Thus, the SAL measures the probability of a sterilization method resulting in a non-sterilized product. The calculation to determine SAL is described in more detail in the below examples. For example, it has been found that a method of exposing the antiseptic solution to a temperature of 100° C. for about 50 minutes, a temperature of 105° C. for about 17 minutes, or 110° C. for about 6 minutes would each have a SAL of at least $10^{-6}$ (i.e., a $1/1,000,000$ chance that a viable microbe will be present in a sterilized solution).

As noted above, after the sterilization time ends, the solution may be cooled. For example, it may take about 10 to about 40 minutes to cool the antiseptic solution following the sterilization time. The time can be shortened using a cooling device. This additional time correlates with the particular sterilization temperature. For examples, a higher sterilization temperature (e.g., 125° C.) as compared to a lower sterilization (e.g., 85° C.) would take longer to return to room temperature after sterilization. Thus, the overall processing time, including cool down, may include an additional about 10 to about 20 minutes longer than the sterilization time.

It is within the scope of the invention that any machine capable of heating the antiseptic solution to the sterilization temperature and maintaining the solution at the sterilization temperature for the sterilization time may be used, while preferably limiting the ramp up time. Example equipment that may include a cascading water sterilizer. When using the cascading water sterilizer the ramp up time may be about 15 minutes, while the cool down time may be about 25 minutes. The cascading water sterilizer provides a constant stream of water which heats the solution to the sterilization temperature, maintains the sterilization temperature over the entirety of the sterilization time, and finally cools the solution.

As provided above, example combinations of sterilization time and sterilization temperature that provide a sterilized solution with sufficient purity to satisfy regulatory requirement are as follows. For a sterilization temperature of about 85° C., the sterilization time may be from about 9 hours to about 19 hours. For a sterilization temperature of about 95° C., the sterilization time may be at least about 1.5 hours and up to about 6.5 hours. For a sterilization temperature of about 105° C., the sterilization time may be from about 17 minutes to about 2.5 hours. For a sterilization temperature of about 110° C., the sterilization time may be at least about 6 minutes and up to about 90 minutes. For a sterilization temperature of about 115° C., the sterilization time may be from about 3 minutes to about 55 minutes. For a sterilization temperature of about 120° C., the sterilization time may be at least about 2 minutes and up to about 35 minutes. For a sterilization temperature of about 125° C., the sterilization time may be from about 1 minute to about 22 minutes. For a sterilization temperature of about 130° C., the sterilization time may be at least about 1 minute and up to 14 minutes. For a sterilization temperature of about 135° C., the sterilization time may be from about 1 minute to about 9 minutes.

Figure 1:
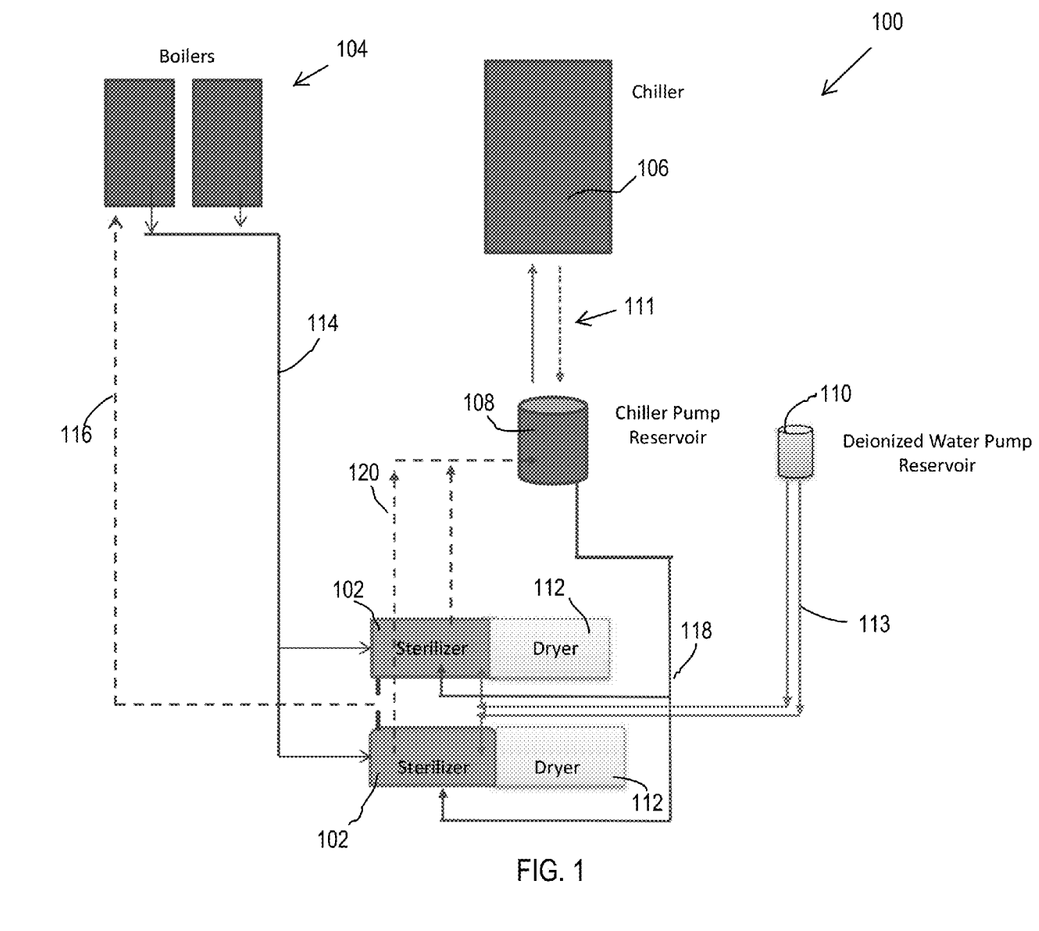
FIG. 1 is a schematic flowchart of an example sterilization system in accordance with certain aspects of the present invention.

FIG. 1 shows a schematic flowchart of an example sterilization system 100. Generally, the sterilization system 100 may include one or more sterilizer units 102 (e.g., cascading waterfall units), boilers 104, a chiller 106, a chiller pump reservoir 108, a deionized water pump reservoir 110, and dryers 112. In operation, prior to the sterilization process, a plurality of containers are filled with antiseptic solution. The containers may have various sizes for holding different volumes of solution. For example, a container may be sized to hold 0.67, 1, 1.5, 3, 10.5, and 13 mL of antiseptic solution (in the case of 13 mL containers, in some aspects, two are placed into a single applicator for a total of 26 mL of solution in a single applicator). The containers having the antiseptic solution are then loaded vertically standing upright into cassettes. The cassettes may be made of metal. The cassettes may be configured to be filled directly from solution filling machines. The cassettes may also be configured to plug directly into assembly equipment so that the containers are transferred with minimal human handling. In an aspect, each cassette may weigh less than 20 lbs when completely loaded to minimize the ergonomic risk associated with manual handling.

In a preferred aspect, all of the containers in the cassettes are the same size during a particular sterilization process because the sterilization conditions will vary based on the size and number of the containers. The number of containers per cassette will vary depending on which size container is being used and the size of the cassette. For a larger container, for example 13 mL, about 300 to 350, more preferably about 330 containers may be loaded into a single cassette. For smaller containers, such as 0.67 mL, about 1800 to 2200, more preferably about 2000 containers may be loaded into a single cassette. Multiple cassettes may then be loaded into a rack that holds a plurality of cassettes. For example, 1 to 144 cassettes may be placed in a single rack. Thus, for the smaller containers each rack may have up to 200,000 containers and for the larger containers each rack may have up to about 50,000 containers. The following chart provides some example implementations of various containers in the sterilization system:

| Container volume | container/ cassette | max cassettes per rack | max cassettes per cycle | approx. containers per rack | approx. containers per cycle | Approximate volume of solution (L) |
|---|---|---|---|---|---|---|
| 0.67 mL | 1,800 | 120 | 240 | 216,000 | 432,000 | 289 |
| 1 mL | 1,700 | 120 | 240 | 204,000 | 408,000 | 408 |
| 1.5 mL | 1,700 | 120 | 240 | 204,000 | 408,000 | 612 |
| 3 mL | 1,600 | 84 | 168 | 134,400 | 268,800 | 806 |
| 10.5 mL | 330 | 144 | 288 | 47,520 | 95,040 | 998 |
| 13 mL | 330 | 144 | 288 | 47,520 | 95,040 | 1,236 |

The system may be capable of sterilizing 1 or 2 racks at a time, although much larger systems are also possible. Once the cassettes are loaded into the racks, each rack may be placed into a sterilizing chamber of one of the sterilizing units 102. With multiple sterilizing units 102, multiple sterilizing processes may occur at the same time.

Once placed in the sterilizing units 102, the sterilizing process may begin. Deionized water from the deionized water pump reservoir 110 may be pumped through the input lines 113 into the chamber of each sterilizing unit 102. A computer control system having a specially programmed computer may be used to control and run the process. The computer control may be specially programmed so that the operating parameters will differ based on the type of containers being sterilized, among other parameters. The computer controller will instruct the system to provide the proper level of deionized water into the chamber for the particular product being sterilized. The deionized water is then circulated within the chamber.

Simultaneously with the circulation of the deionized water in the chamber, the computer control system may open valves to allow steam from the boilers 104 into the sterilizer units 102 via input lines 114. The steam does not enter the chamber directly, but passes into a heat exchanger. The steam passes through the heat exchanger as does the deionized water, allowing for heat exchange between them without direct interaction between the steam and deionized water. The steam condensate, originating from the boilers 104, now cooler due to the heat exchange, may exit the heat exchanger and return to the boilers 104 via return lines 116. The cycle of heat exchange continues until the system measures that the temperature of the circulating, deionized water is at the appropriate predetermined sterilization temperature. The system then precisely controls the input of steam to maintain the sterilization temperature, such as by actuating the appropriate valves.

During this same time that the heat exchange is occurring, the deionized water in the chamber is being continuously circulating within the chamber such that the deionized water falls over the containers in the cassettes (hence, the term cascading waterfall). This process heats the antiseptic solution within the containers.

As shown in FIG. 1, more than one boiler (e.g., two) may be used to provide the steam. Two boilers may be implemented in series to provide redundancy if one of the boilers fails. Alternatively, one large boiler may be implemented.

Once the sterilization time has been completed the computer control system will then start the cooling down process. The cooling process is analogous to the heating process, except that chilled water is used where steam is used in the heating process. For example, cooling water may be chilled via the chiller 106. The chilled water may travel between the chiller pump reservoir 108 via input/return lines 111 so that chilled water is ready for use. The chilled water may travel from the chiller pump reservoir 108 to heat exchanger of the sterilizing units 102 via input lines 118. As described above with respect to the steam heat exchange, the chilled water may exchange heat with the deionized water, thereby cooling the deionized water and heating the cooling water. During this cooling heat exchange process, the deionized water continues to circulate within the chamber an fall over the containers. Following the heat exchange, the now-warmed cooling water may travel back to the chiller pump reservoir 108 and into the chiller 106 via lines 120/111. The cooling cycle continues until the deionized water in the chamber has reached the desired temperature (e.g., room temperature).

Upon completing the cooling of the deionized water, and after sufficient time has passed for the antiseptic solution to have cooled, the deionized water may be drained so that opening of the chamber doors will not leak water when opened. Next, the racks of now-sterilized containers may travel down a conveyer to the dryers 112. The dryers 112 are used to dry the outside of the containers which have become wet from the deionized water in the sterilization process. Heated, dehumidified air may be used to rapidly dry the containers. In one example aspect, the containers with solution may be dried at air temperatures of less than 50° C. within approximately 1 hour. This allows the containers to be ready for direct placement into an antiseptic applicator, which would not be possible if the containers were wet. Furthermore, it has been found that the drying temperature and time period does not unsuitably degrade the antiseptic molecule within the container. The dryers may employ large dehumidifiers to pull the water out of the air that is used to dry the containers. Without the dehumidifiers, one would expect much higher temperatures and/or longer drying times. The drying cycle may be optimized for various product loads based on volume, packing density (e.g., number of containers per cassette), and spacing of containers with solution, among other factors.

The cascading waterfall sterilizer units may be placed below grade so that they may be loaded without the need for elevated loaded equipment. Each of the sterilizing units may include a conductivity sensor to measure a change in water conductivity based on the amount of antimicrobial molecule present in the water that is being used to sterilize the containers with solution. By detecting the presence of antimicrobial molecules in the sterilizing water, the operator may indirectly measure the amount of container breakage during each sterilization process. In other words, because antimicrobial solution is released into the circulating water when a container breaks, the concentration of drug product in the water allows the operator to estimate the number of containers broken during the process. The system may be configured such that sterilizing water may be drained directly to a hazardous waste if the conductivity sensor indicates excessive quantities of (e.g., above a predetermined threshold concentration) antimicrobial in the water.

The system may further include pallet jacks for use with racks. Pallet jacks may be desirable because the racks are preferably made of stainless steel and weigh a few hundred pounds. As the cassettes are also preferably made of stainless steel, the weight of the cassettes plus the and weight of the containers means that each rack may weigh in excess of 2000 lbs. Spark resistant electric pallet jacks are preferred because of the potential ignition risks associated with the isopropyl alcohol present inside the containers.

The system may also include a bladder tank (not shown) between that deionized pump reservoir and the sterilizer. The bladder tank may be filled with deionized water up to a predetermined pressure. Then, the pump may be turned off and the bladder tank maintains a pressure in the line, thereby preventing damage to the pump. When the chambers open valves to fill prior to initiating a sterilization cycle, the pressure in the line supplies water immediately. The pump, detecting the pressure drop in the bladder tank, proceeds to supply water as needed until the bladder tank pressure returns to the predetermined point.

As noted above, a program (i.e., a specially programmed computer) may be used to control the entire sterilization system. The program may allow for the computer to communicate with the dryers to receive and transmit data, among other components of the system, as described above.

EXAMPLES

A sample of antiseptic solution of 70% v/v isopropanol, 30% v/v water, and 2.0% w/v chlorhexidine gluconate contained in a glass ampoule was tested in each of the following examples. An inoculum of greater than 1,000,000 but less than 10,000,000 test spores of Geobacillus stearothermophilus were inserted and sealed into the container. In the following examples, a 10 mL sample of antiseptic solution at room temperature was placed in either a water or oil bath (water bath for temperatures of ≤95° C.; oil bath for temperatures≥100° C.) having a preset temperature (i.e., the sterilization temperature). The ampoule containing chlorhexidine gluconate solution and test spores was placed in the heating medium. The sample with test spores was removed at a particular time (i.e., the sterilization time), allowed to cool to room temperature, then tested and incubated over a seven day period for bacterial growth. Samples of antiseptic solution also stored at the preset temperature were tested for degradation of chlorhexidine gluconate. The 7-day bacterial growth testing followed the procedures described in U.S. Pharmacopeial Convention (USP) Chapter 55 "Biological Indicators—Resistance Performance Tests," USP 36; Official from May 1, 2013. Tables 1-6 show the data collected for purity and sterility of a chlorhexidine gluconate solution that was 98.67% pure prior to the heat treatment. The purity percent values listed in the tables are the absolute purity of the chlorhexidine gluconate after heat treatment and cooling to ambient temperature. The Δpurity percent values are the percentage point change relative to the baseline purity. For example, in Table 1, at 78° C. and 4 hours the purity of chlorhexidine gluconate was 98.05%, which is a 0.62% percentage point change from the initial purity of 98.67%.

TABLE 1

78° C., Initial Purity 98.67%, water bath

| | Time (hours) | | | | | |
|---|---|---|---|---|---|---|
| | 4 | 6 | 8 | 16-18 | 24 | 48 |
| Purity (%) | 98.05% | 97.86% | 97.61% | 96.70% | 95.85% | 92.84% |
| ΔPurity (%) | 0.62% | 0.81% | 1.05% | 1.97% | 2.82% | 5.82% |
| Sterility (days) | Not sterile Growth at 1 day | | Not sterile Growth at 2 days | Not sterile Growth at 2 days | | Sterile 7 days |

TABLE 2

80° C., Initial Purity 98.67%, water bath

| | Time (hours) | | | | | |
|---|---|---|---|---|---|---|
| | 6 | 8 | 10 | 16-18 | 24 | 48 |
| Purity (%) | 97.85% | 97.50% | 97.26% | 96.49% | 95.14% | 91.55% |
| ΔPurity (%) | 0.81% | 1.17% | 1.41% | 2.18% | 3.53% | 7.12% |

TABLE 3

82° C., Initial Purity 98.67%, water bath

| | Time (hours) | | | | | | |
|---|---|---|---|---|---|---|---|
| | 4 | 6 | 8 | 10 | 16-18 | 24 | 48 |
| Purity (%) | 97.72% | 97.38% | 97.03% | 96.73% | 95.70% | 94.31% | 89.63% |
| ΔPurity (%) | 0.94% | 1.29% | 1.64% | 1.94% | 2.97% | 4.35% | 9.03% |
| Sterility (days) | Not sterile Growth at 1 day | | Not sterile Growth at 1 day | | Sterile 7 days | | Sterile 7 days |

TABLE 4

85° C., Initial Purity 98.67%, water bath

| | Time (hours) | | | | | | |
|---|---|---|---|---|---|---|---|
| | 2 | 4 | 6 | 8 | 10 | 16-18 | 24 | 48 |
| Purity (%) | 98.11% | 97.46% | 97.09% | 96.60% | 96.21% | 93.96% | 92.11% | 85.54% |
| ΔPurity (%) | 0.56% | 1.20% | 1.58% | 2.07% | 2.46% | 4.70% | 6.56% | 13.13% |
| Sterility (days) | Not sterile Growth at 1 day | | | Sterile 7 days | | Sterile 7 days | | Sterile 7 days |

TABLE 5

90° C., Initial Purity 98.67%, water bath

| | Time (hours) | | | | | | | |
|---|---|---|---|---|---|---|---|---|
| | 2 | 4 | 6 | 8 | 10 | 16-18 | 24 | 48 |
| Purity (%) | 97.50% | 96.66% | 95.79% | 94.88% | 94.37% | 91.59% | 87.51% | 73.67% |
| ΔPurity (%) | 1.17% | 2.01% | 2.88% | 3.79% | 4.30% | 7.08% | 11.16% | 25.00% |

TABLE 6

95° C., Initial Purity 98.67%, water bath

| | Time (hours) | | | | | | | | | | |
|---|---|---|---|---|---|---|---|---|---|---|---|
| | 0.25 | 0.5 | 1.25 | 2 | 4 | 6 | 8 | 10 | 16-18 | 24 | 48 |
| Purity (%) | | | | 97.05% | 95.53% | 94.74% | 92.77% | 91.04% | | 77.97% | 49.72% |
| ΔPurity (%) | | | | 1.62% | 3.14% | 3.93% | 5.89% | 7.63% | | 20.70% | 48.95% |
| Sterility (days) | Not sterile Growth at 1 day | Not sterile Growth at 4 day | Sterile 7 days | | Sterile 7 days | | Sterile 7 days | | Sterile 7 days | | Sterile 7 days |

Additional experiments were performed in an oil bath to test purity changes at 105° C. and 115° C. Glass ampoules containing the antiseptic solution were subjected to the sterilization times and sterilization temperatures shown in Table 7 and Table 8 using an oil bath. The change in % purity for the antiseptic solution after the sterilization time was measured and compared to the initial % purity values. The measurements were taken after the solution returned to ambient temperature.

TABLE 7

105° C. Initial Purity 98.7%, oil bath

| | Time (hours) | | | | |
|---|---|---|---|---|---|
| | 0.25 | 0.5 | 0.833 | 1 | 1.5 |
| Purity (%) | 98.3% | 98.0% | 97.2% | 96.9% | 95.7% |
| ΔPurity (%) | 0.40 | 0.80 | 1.58 | 1.89 | 3.03 |

TABLE 8

115° C., Initial Purity 98.7% oil bath

| | Time (hours) | | | | |
|---|---|---|---|---|---|
| | 0.1667 | 0.333 | 0.5 | 0.667 | 0.833 |
| Purity (%) | 97.9% | 97.1% | 96.2% | 95.2 | 94.3% |
| ΔPurity (%) | 0.82 | 1.61 | 2.59 | 3.54 | 4.50 |

The above data was then used to prepare an Arrhenius equation using the standard method in the art. The use of an Arrhenius equation is a well-known and accepted method of modeling temperature dependence on reaction rate. Using the Arrhenius equation, the following predicted values for purity were obtained:

TABLE 9

Predicted Purity Using Arrhenius Equation

| Sterilization Temperature (° C.) | Maximum Sterilization Time to maintain a specified purity change (min) | | | |
|---|---|---|---|---|
| | 2% | 3% | 4% | 5% |
| 85 | N/A | 670 | 900 | 1123 |
| 90 | 260 | 390 | 525 | 654 |
| 95 | 155 | 230 | 310 | 386 |
| 100 | 92 | 140 | 185 | 231 |
| 105 | 55 | 85 | 113 | 140 |
| 110 | 35 | 52 | 70 | 86 |
| 115 | 22 | 32 | 43 | 54 |
| 120 | 14 | 20 | 27 | 34 |
| 125 | 9 | 13 | 17.5 | 21.5 |
| 130 | 5.5 | 8.5 | 11 | 14 |
| 135 | 3.7 | 5.5 | 7.3 | 9.1 |

The measured impact of various sterilization temperatures and sterilization times on the characteristics of the antiseptic are shown below. Table 10 summarizes the change in % purity for the chlorhexidine gluconate after exposure to various sterilization temperatures and sterilization times. The percent change in purity is made by comparing the purity of solution prior to the ramp up time (i.e., prior to the process of bringing the solution up to the sterilization temperature) with the purity of solution after the cool down time (i.e., after the solution returns ambient temperature). 'W' indicates that the sterilization temperature and sterilization time would result in the change of purity of not more than 2%. The 'X', 'Y' and 'Z' indicate that the sterilization temperature and sterilization time would result in a change of purity of not more than 3%, 4% and 5%, respectively. Finally, an 'A' indicates that the sterilization temperature and sterilization time would result in the change of purity of greater than 5%.

TABLE 10

Effect of Heat and Temperature on Chemical Stability

| | | Sterilization Time (hours) | | | | | | | | | | | | | | |
|---|---|---|---|---|---|---|---|---|---|---|---|---|---|---|---|---|
| | | 0.17 | 0.25 | 0.33 | 0.5 | 0.67 | 0.83 | 1 | 1.5 | 2 | 4 | 6 | 8 | 10 | 16-18 | 24 |
| Sterilization Temp (° C.) | 78 | | | | | | | | | | W | W | W | | W | X |
| | 80 | | | | | | | | | | W | W | W | X | Y | |
| | 82 | | | | | | | | | W | W | W | W | X | Z | |
| | 85 | | | | | | W | W | W | X | X | Z | A | | | |

TABLE 10-continued

Effect of Heat and Temperature on Chemical Stability

| | Sterilization Time (hours) | | | | | | | | | | | | | |
|---|---|---|---|---|---|---|---|---|---|---|---|---|---|---|
| | 0.17 | 0.25 | 0.33 | 0.5 | 0.67 | 0.83 | 1 | 1.5 | 2 | 4 | 6 | 8 | 10 | 16-18 | 24 |
| 90 | | | | | | | | | W | X | X | Y | Z | A | A |
| 95 | | | | | | | | | W | Y | Y | A | A | | A |
| 105 | | W | | W | | W | W | Y | | | | | | | |
| 115 | W | | W | X | Y | Z | | | | | | | | | |

KEY: W = the solution had a change in purity of not more than 2%
X = the solution had a change in purity of not more than 3%
Y = the solution had a change in purity of not more than 4%
Z = the solution had a change in purity of not more than 5%
A = the solution had a change in purity above 5%

Table 11 summarizes the measured sterility of an antiseptic solution containing greater than or equal to 1,000,000 but less than 10,000,000 test spores of Geobacillus stearothermophilus after exposure to various sterilization temperatures sterilization times.

TABLE 11

Effect of Heat and Temperature on Sterility

| | | Sterilization Time (hours) | | | | | | | | | | | | |
|---|---|---|---|---|---|---|---|---|---|---|---|---|---|---|
| | | 0.05 | 0.1 | 0.25 | 0.4 | 0.5 | 0.7 | 1.25 | 4 | 6 | 8 | 18 | 24 | 48 |
| Sterilization | 78 | | | | | | | | | | N | N | N | Y |
| Temp | 82 | | | | | | | | | | N | N | Y | Y |
| (° C.) | 85 | | | | | | | | | | N | Y | Y | Y |
| | 95 | | N | | N | | Y | Y | | | Y | Y | | Y |
| | 100 | | N | N | N | Y | | | | | | | | |
| | 105 | | N | Y | | | | | | | | | | |
| | 110 | Y | Y | | | | | | | | | | | |

KEY: Y = the solution was sterile as shown by absence of viable bacterial spores
N = the solution was not sterile as evidenced by growth of viable bacterial spores As shown in the above tables when varying sterilization time and temperature, there is a particular window where the treated antiseptic solution is sterile and has change in purity of less than a certain percentage, for example 5%. It should be noted that because the above data is a threshold analysis, one can extrapolate the results for other sterilization times. Once it is found that the change in purity is at least 5% at particular temperature and time, it can be presumed that longer sterilization times at the same temperature will further degrade the solution. It can also be presumed that all samples starting with the same initial purity value which are sterilized for shorter times at the same temperature below the time found to have lower than a 5% change in purity will also have change in purity lower than 5%. For example, the sample tested at 95° C. for 4 hours had 95.53% purity, while the sample tested at 95° C. for 6 hours had 94.74%. Accordingly, it can be extrapolated that all sterilization times greater than 6 hours at 95° C. will have less than 95.74% purity, while all sterilization times less than 4 hours at 95° C. will have at least 95.53% purity. Similarly, with respect to the USP seven-day sterility test, once it is found that a sample has seven-day sterility at a particular sterilization temperature and time, it can be presumed that longer sterilization time at the same temperature will also exhibit seven day sterility (i.e., long term sterility). Thus, it can presumed that all samples sterilized for longer times at the same temperature beyond the time found to have seven-day sterility will also have seven day sterility. It can also be presumed that all samples sterilized at shorter times but at the same temperature compared to a sample found not to have seven-day sterility will also not have seven day sterility. For example, the sample tested at 95° C. for 1.25 hours was sterile after seven days, while the sample tested at 95° C. for 0.5 hours had bacterial growth within four days (i.e., did not have seven day sterility). Accordingly, it can be extrapolated that all sterilization times greater than 1.25 hours at 95° C. will be sterile after seven days while all sterilization times less than 0.5 hours at 95° C. will have bacterial growth within seven days.

The same can be done for other threshold values (e.g., changes in purity below or higher than 5%, such as 2%, 3%, and 4%).

In addition to above testing, further testing was conducted to determine at what time the Sterility Assurance Level (SAL) of $10^{-6}$ can be reached at a certain temperature. The USP 55 "Biological Indicators—Resistance Performance Tests" procedures were followed to determine the SAL. Greater than or equal to 1,000,000 test spores of Geobacillus stearothermophilus, but less than 10,000,000, were inserted into a 1 mL sample of antiseptic solution comprising 70% v/v isopropanol in water and 2.0% w/v chlorhexidine gluconate. The samples were tested at 100° C., 105° C., and 110° C. for various times. Ten samples were tested at each time point. The results were as follows:

TABLE 12

Sterility Test Results for SAL Testing

| 100° C. | | 105° C. | | 110° C. | |
|---|---|---|---|---|---|
| Time (min) | Result (# positive) | Time (min) | Result (# positive) | Time (min) | Result (# positive) |
| 10 | 10 | 6 | 10 | 3 | 10 |
| 15 | 9 | 7.5 | 5 | 3.5 | 0 |

TABLE 12-continued

Sterility Test Results for SAL Testing

| 100° C. | | 105° C. | | 110° C. | |
|---|---|---|---|---|---|
| Time (min) | Result (# positive) | Time (min) | Result (# positive) | Time (min) | Result (# positive) |
| 20 | 3 | 9 | 2 | 4 | 1 |
| 25 | 3 | 10 | 0 | 4.5 | 0 |
| 30 | 2 | 12 | 2 | 5 | 0 |
| 35 | 3 | 14 | 0 | 6 | 0 |
| 40 | 0 | 16 | 0 | 7 | 0 |
| 50 | 0 | 20 | 0 | 8 | 0 |
| | | 24 | 0 | 10 | 0 |
| | | | | 12 | 0 |
| | | | | 14 | 0 |

The above results are expressed as the number of positives recorded out of ten samples tested. For example, "10" means 10 samples out of 10 samples tested positive for microbes (non-sterile). The above data was then used to calculate the "D-values," in accordance with USP 55 procedures. The term D-value has the normal meaning as used in microbiology. Specifically, it refers to decimal reduction time and is the time required at a certain temperature to kill 90% of the organisms being studied. Thus after a colony is reduced by 1 D, only 10% of the original organisms remain, i.e., the population number has been reduced by one decimal place in the counting scheme. D-values can be calculated using the Holcomb-Spearman-Karber Method (HSK), which is a data analysis known in the art (see USP 55 procedures and Block, Seymour S. "Disinfection, Sterilization, and Preservation." Philadelphia, Pa.: Lippincott Williams & Wilkens, 120-122. 2001). Applying the HSK method to the above Table 12 data, the resulting D-values were calculated along with upper and lower confidence limits:

TABLE 13

D-Values

| Temp (° C.) | D-value (min) | Lower Confidence 95% (min) | Upper Confidence 95% (min) |
|---|---|---|---|
| 84 | 51 | 44 | 59 |
| 100 | 3.55 | 3.06 | 4.05 |
| 105 | 1.29 | 1.16 | 1.41 |
| 110 | 0.50 | 0.48 | 0.51 |

The D-values can be used to calculate a sterility assurance Level (SAL) (see USP 55 procedures). SAL is a term used in microbiology to describe the probability of a single unit being non-sterile after it has been subjected to a sterilization process. A $10^{-6}$ SAL means there is a 1/1,000,000 chance that a single viable microbe will remain in sterilized items. By extrapolating the log reduction rates following an extreme, artificially high initial contamination, the sterilization procedure must encompass 12 log increments (multiplying the D-value by 12), overkill conditions, in order to verify an SAL of $10^{-6}$. Erring on the side of caution, the upper confidence limit D-values were used to calculate the following time to achieve $10^{-6}$ SAL:

TABLE 14

SAL $10^{-6}$ Time

| Temp (° C.) | Time to achieve SAL $10^{-6}$ (minutes) |
|---|---|
| 84 | 612.00 |
| 100 | 48.58 |
| 105 | 16.97 |
| 110 | 6.17 |

Thus, as indicated in Table 14, exposing the antiseptic solution to a temperature of 100° C. for about 48.58 minutes, a temperature of 105° C. for about 16.97 minutes, or 110° C. for about 6.17 minutes would each have a SAL of $10^{-6}$ (i.e., a 1/1,000,000 chance that a viable microbe will be present following the sterilization process).

Using standard mathematical modeling, the above four D-value data points from Table 14 were used to prepare a exponential predictive function having the following formula:

$$y = 1{,}553{,}000{,}000 \cdot e^{(-0.1747x)} \tag{I}$$

where y is time in minutes and x is temperature in degrees Celsius. Thus, Formula (I) indicates at a given temperature the minimum time for achieving at least a $10^{-6}$ SAL. Using Formula (I), the following predictive data points were generated:

TABLE 15

Predictive SAL $10^{-6}$ Time

| Temp (° C.) | Time to achieve SAL $10^{-6}$ (min) |
|---|---|
| 85 | 552.23 |
| 95 | 96.25 |
| 115 | 2.92 |
| 120 | 1.22 |
| 125 | 0.51 |
| 130 | 0.21 |
| 135 | 0.09 |

The times found in Tables 14 and 15 have been rounded as follows in Table 16:

TABLE 16

Rounded SAL $10^{-6}$ Time

| Temp (° C.) | Time to achieve SAL $10^{-6}$ (min) |
|---|---|
| 85 | 552 |
| 95 | 96 |
| 100 | 48 |
| 105 | 17 |
| 110 | 6.2 |
| 115 | 3 |
| 120 | 2 |
| 125 | 1 |
| 130 | 1 |
| 135 | 1 |

Figure 2:
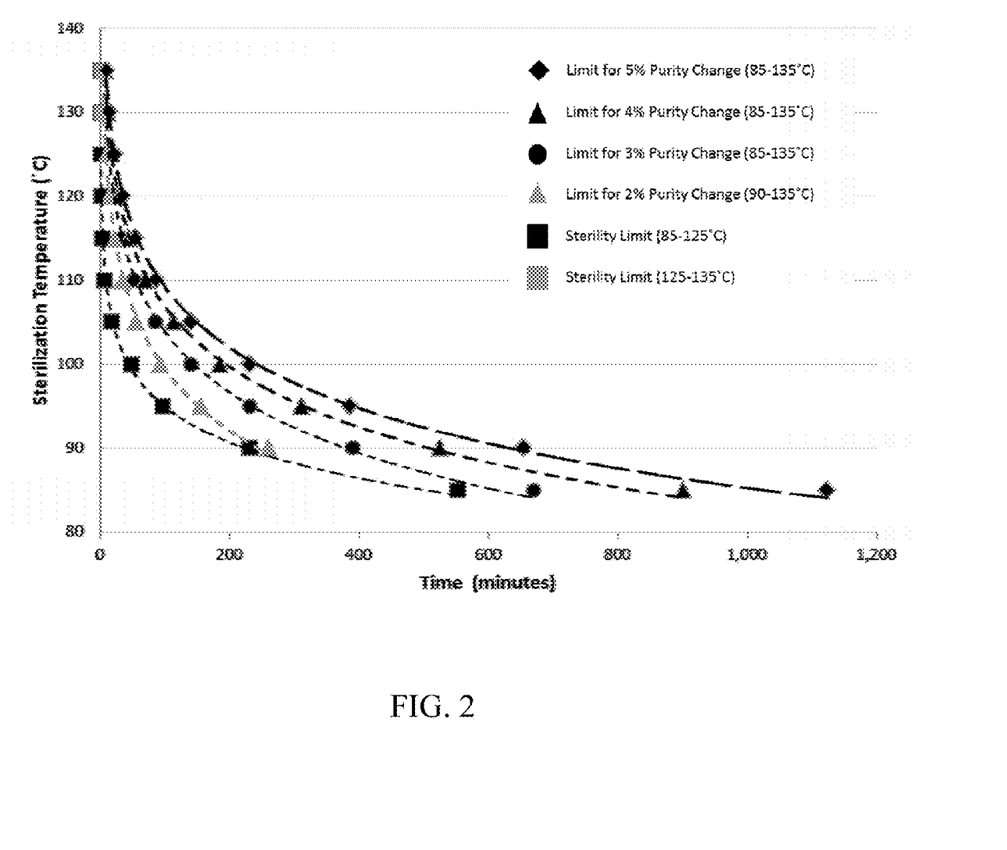
FIG. 2 is a graph of sterilization temperature and sterilization time data in accordance with certain aspects of the present invention.

The rounded data points are plotted in FIG. 2. FIG. 2 illustrates the sterilization times and temperatures fit to functions which capture the parameter space (time and temperature) to maintain a specific change in purity following the sterilization process (area between curves). The data points in FIG. 2 include data points from Table 9 and Table 16 above. The black squares represent the data points from 85° C. to 120° C. where the corresponding times were sterile. The grey squares represent data points from 125° C. to 135° C. where the corresponding times were sterile. The following natural log formula was fitted to the square data points from 85° C. to 125° C.:

$$y=-6.14 \cdot \ln x+123.2 \text{ for } 1 \leq x \leq 552 \quad (II)$$

where y is the temperature in degrees Celsius and x is the time in minutes. From 125° C. to 135° C., the time x is a constant 1 minute.

The data points found in Table 9 above were also plotted in FIG. 1. The black diamonds represent the data points from 85° C. to 135° C. where the corresponding times had at most a percent change in purity of 5%. The black triangles represent the data points from 85° C. to 135° C. where the corresponding times had at most a percent change in purity of 4%. The black circles represent data points from 85° C. to 135° C. where the corresponding times had at most a % change in purity of 3%. The grey triangles represent data points from 90° C. to 135° C. where the corresponding times had at most a percent change in purity of 2%. There was no time at 85° C. where the solution would have at most a percent change in purity of 2%. The following natural log formula was fitted to the black diamond data points (i.e., the points having at most 5% change in purity):

$$y=-10.38 \cdot \ln x+156.9 \text{ for } 9.1 \leq x \leq 1123 \quad (III)$$

The following natural log formula was fitted to the black triangle data points (i.e., the points having at most 4% change in purity):

$$y=-10.37 \cdot \ln x+154.6 \text{ for } 7.3 \leq x \leq 900 \quad (IV)$$

where y is the temperature in degrees Celsius and x is the time in minutes. The following natural log formula was fitted to the black circle data points (i.e., the points having at most 3% change in purity):

$$y=-10.4 \cdot \ln x+151.7 \text{ for } 5.5 \leq x \leq 670 \quad (V)$$

where y is the temperature in degrees Celsius and x is the time in minutes. The following natural log formula was fitted to the grey triangle data points (i.e., the points having at most 2% change in purity):

$$y=-10.6 \cdot \ln x+148.3 \text{ for } 3.7 \leq x \leq 260 \quad (VI)$$

where y is the temperature in degrees Celsius and x is the time in minutes.

As can be seen in FIG. 2, the area above Formula (II) but below formula (III), within the temperature range of 85° C. to 125° C., represents temperature and time combinations that provide a sterile solution with at most a 5% change in purity. This area can thus be presented by the following relationship:

$$y \geq -6.14 \cdot \ln x+123.2 \text{ for } 1 \leq x \leq 552$$

and $$y \leq -10.38 \cdot \ln x+156.9 \text{ for } 21.5 \leq x \leq 1123,$$

where y is temperature in degrees Celsius and x is time in minutes. Similarly, within the temperature range of 125° C. to 135° C., the area above the constant line x=1 and below formula (III) represents temperature and time combination that provide a sterile solution with a most 5% change in purity. This area can be presented by the following relationship:

$$x \geq 1$$

and $$y \leq -10.38 \cdot \ln x+156.9 \text{ for } 9.1 \leq x \leq 21.5$$

where y is the temperature in degrees Celsius and x is time in minutes.

As can be seen in FIG. 2, the area above Formula (II) but below formula (IV), within the temperature range of 85° C. to 125° C., represents temperature and time combinations that provide a sterile solution with at most a 4% change in purity. This area can thus be presented by the following relationship:

$$y \geq -6.14 \cdot \ln x+123.2 \text{ for } 1 \leq x \leq 552$$

and $$y \leq -10.37 \cdot \ln x+154.6 \text{ for } 17.5 \leq x \leq 900,$$

where y is temperature in degrees Celsius and x is time in minutes. Similarly, within the temperature range of 125° C. to 135° C., the area above the constant line x=1 and below formula (IV) represents temperature and time combination that provide a sterile solution with a most 4% change in purity. This area can be presented by the following relationship:

$$x \geq 1$$

and $$y \leq -10.37 \cdot \ln x+154.6 \text{ for } 7.3 \leq x \leq 17.5$$

where y is the temperature in degrees Celsius and x is time in minutes.

As can be seen in FIG. 2, the area above Formula (II) but below formula (V), within the temperature range of 85° C. to 125° C., represents temperature and time combinations that provide a sterile solution with at most a 3% change in purity. This area can thus be presented by the following relationship:

$$y \geq -6.14 \cdot \ln x+123.2 \text{ for } 1 \leq x \leq 552$$

and $$y \leq -10.4 \cdot \ln x+151.7 \text{ for } 13 \leq x \leq 670$$

where y is temperature in degrees Celsius and x is time in minutes. Similarly, within the temperature range of 125° C. to 135° C., the area above the constant line x=1 and below formula (V) represents temperature and time combination that provide a sterile solution with a most 3% change in purity. This area can be presented by the following relationship:

$$x \geq 1$$

and $$y \leq -10.4 \cdot \ln x+151.7 \text{ for } 5.5 \leq x \leq 13,$$

where y is the temperature in degrees Celsius and x is time in minutes.

As can be seen in FIG. 2, the area above Formula (II) but below formula (VI), within the temperature range of 90° C. to 125° C., represents temperature and time combinations that provide a sterile solution with at most a 2% change in purity. This area can thus be presented by the following relationship:

$$y \geq -6.14 \cdot \ln x+123.2 \text{ for } 1 \leq x \leq 552$$

and $$y \leq -10.6 \cdot \ln x+148.3 \text{ for } 9 \leq x \leq 260$$

where y is temperature in degrees Celsius and x is time in minutes. Similarly, within the temperature range of 125° C.

to 135° C., the area above the constant line x=1 and below formula (VI) represents temperature and time combination that provide a sterile solution with a most 2% change in purity. This area can be presented by the following relationship:

$$x \geq 1$$

and $$y \leq -10.6 \cdot \ln x + 148.3 \quad 3.7 \leq x \leq 9$$

where y is the temperature in degrees Celsius and x is time in minutes.

While aspects of the present invention have been described in connection with illustrative implementations, it will be understood by those skilled in the art that variations and modifications of the aspects described above may be made without departing from the scope hereof. Other variations will be apparent to those skilled in the art from a consideration of the specification or from a practice along the lines as disclosed herein.

The invention claimed is:

1. A method for sterilizing antiseptic solution, the method comprising:
   providing a plurality of containers containing the antiseptic solution, the antiseptic solution having:
      an antimicrobial compound selected from the group consisting of a bis-(dihydropyridinyl)-decane derivative and a biguanide; and
      an initial purity;
   selecting a sterilization temperature from about 85° C. to about 135° C. and a sterilization time from about 1 minute to about 19 hours;
   heating the antiseptic solution in the plurality of containers to the selected sterilization temperature;
   maintaining the antiseptic solution in the plurality of containers at the sterilization temperature for the selected sterilization time; and
   terminating the heating of the antiseptic solution in the plurality of containers when the selected sterilization time expires,
   wherein after terminating the heating, the antiseptic solution in the plurality of containers has a post-sterilization purity, and
   wherein the sterilization temperature and the sterilization time are selected such that after terminating the heating, the antiseptic solution in the plurality of containers is sterile and said solution in the plurality of containers has a post-sterilization purity of at least about 92% and a percentage point change in purity from the initial purity to the post-sterilization purity of at most about 5%.

2. The method of claim 1, wherein the antiseptic compound is a biguanide.

3. The method of claim 2, wherein the selected sterilization time and selected sterilization temperature satisfy the following relationship:

a) $85° C. \leq y < 125° C.$, $y \geq -6.14 \cdot \ln x + 123.2$ for $1 \leq x \leq 552$, and $y \leq -10.38 \cdot \ln x + 156.9$ for $21.5 \leq x \leq 1123$; or b) $125° C. \leq y \leq 135° C.$, $x \geq 1$ and $y \leq -10.38 \cdot \ln x + 156.9$ for $9.1 \leq x \leq 21.5$, wherein y is the sterilization temperature and x is the sterilization time in minutes.

4. The method of claim 2, wherein the selected sterilization time and selected sterilization temperature satisfy the following relationship:

a) $85° C. \leq y < 125° C.$, $y \geq -6.14 \cdot \ln x + 123.2$ for $1 \leq x \leq 552$, and $y \leq -10.37 \cdot \ln x + 154.6$ for $17.5 \leq x \leq 900$, or b) $125° C. \leq y \leq 135° C.$, $x \geq 1$ and $y \leq -10.37 \cdot \ln x + 154.6$ for $7.3 \leq x \leq 17.5$, wherein y is the sterilization temperature and x is the sterilization time in minutes.

5. The method of claim 2, wherein the selected sterilization time and selected sterilization temperature satisfy the following relationship:

a) $85° C. \leq y < 125° C.$, $y \geq -6.14 \cdot \ln x + 123.2$ for $1 \leq x \leq 552$, and $y \leq -10.4 \cdot \ln x + 151.7$ for $13 \leq x \leq 670$, or b) $125° C. \leq y \leq 135° C.$, $x \geq 1$ and $y \leq -10.4 \cdot \ln x + 151.7$ for $5.5 \leq x \leq 13$, wherein y is the sterilization temperature and x is the sterilization time in minutes.

6. The method of claim 2, wherein the selected sterilization time and selected sterilization temperature satisfy the following relationship:

a) $90° C. \leq y < 125° C.$, $y \geq -6.14 \cdot \ln x + 123.2$ for $1 \leq x \leq 552$, and $y \leq -10.6 \cdot \ln x + 148.3$ for $9 \leq x \leq 260$, or b) $125° C. \leq y \leq 135° C.$, $x \geq 1$, and $y \leq -10.6 \cdot \ln x + 148.3$ for $3.7 \leq x \leq 9$ wherein y is the sterilization temperature and x is the sterilization time in minutes.

7. The method of claim 2, wherein the selected sterilization temperature and the selected sterilization time are chosen such that after terminating the heating, the antiseptic solution in the plurality of containers has a post-sterilization purity of at least about 94% and the percentage point change in purity from the initial purity to the post-sterilization purity is at most about 4%.

8. The method of claim 2, wherein the selected sterilization temperature and the selected sterilization time are chosen such that after terminating the heating, the antiseptic solution in the plurality of containers has a post-sterilization purity of at least about 96% and the percentage point change in purity from the initial purity to the post-sterilization purity is at most about 3%.

9. The method of claim 2, wherein the selected sterilization temperature and the selected sterilization time are chosen such that after terminating the heating, the antiseptic solution in the plurality of containers has a post-sterilization purity of at least about 98% and the percentage point change in purity from the initial purity to the post-sterilization purity is at most about 2%.

10. The method of claim 2, wherein:
the antimicrobial compound is chlorhexidine gluconate; and
the antiseptic solution comprises an alcoholic solvent selected from the group consisting of ethanol, isopropanol, and n-propanol.

11. The method of claim 2, wherein the antiseptic solution comprises from about 40% to about 90% v/v isopropanol and from about 0.1% to about 2.5% w/v of the antimicrobial compound, and wherein the antimicrobial compound is chlorhexidine gluconate.

12. The method of claim 2, wherein the antiseptic solution comprises about 70% v/v isopropanol and about 2.0% w/v of the antimicrobial compound, and wherein the antimicrobial compound is chlorhexidine gluconate.

13. The method of claim 2, wherein the sterilization time is from about 6 minutes to about one hour.

14. The method of claim 2, wherein the sterilization temperature is about 95° C. and the sterilization time is from about 1.5 hours to about 6.5 hours.

15. The method of claim 2, wherein the sterilization temperature is about 110° C. and the sterilization time is from about 6 minutes to about 90 minutes.

16. The method of claim 2, wherein the sterilization temperature is about 120° C. and the sterilization time is from about 2 minutes to about 35 minutes.

17. The method of claim 2, further comprising:
providing a cascading water sterilizer that produces a cascading waterfall,
wherein heating the antiseptic solution to the selected sterilization temperature and maintaining the selected sterilization temperature comprises contacting the plurality of containers with the cascading waterfall for the duration of the sterilization time.

18. The method of claim 17, further comprising providing a chiller that produces cooling water, the method further comprising cooling the water of the cascading water sterilizer with the cooling water from the chiller.

19. The method of claim 18, further comprising drying the plurality of containers after cooling the antiseptic solution.

20. The method of claim 17, further comprising providing one or more boilers that produces steam, the method further comprising heating the water of the cascading waterfall sterilizer with the steam from the boiler.

21. The method of claim 17, further comprising measuring a change in conductivity of the water of the cascading water sterilizer and correlating the measured change in conductivity to an amount of antiseptic solution present in the water.

22. The method of claim 17, further comprising placing the plurality of containers into a cassette, placing the cassette into a rack, and transferring the rack into a chamber of the cascading water sterilizer.

23. The method of claim 22, wherein placing the plurality of containers into the cassette comprises vertically positioning the plurality of containers within the cassette.

24. The method of claim 23, wherein the plurality of containers comprise from about 330 to about 2000 containers.

25. The method of claim 23, wherein each of the plurality of containers holds about 0.67 mL to about 3 mL of antiseptic solution and the plurality of containers comprise about 1800 to about 2200 containers.

26. The method of claim 23, wherein each of the plurality of containers holds about 10.5 mL to about 13 mL of antiseptic solution and the plurality of containers comprise from about 300 to about 350 containers.

27. A method for sterilizing antiseptic solution, the method comprising:
providing a plurality of containers containing the antiseptic solution, the antiseptic solution having an initial purity;
selecting a sterilization temperature from about 85° C. to about 135° C. and a sterilization time from about 1 minute to about 19 hours;
heating the antiseptic solution in the plurality of containers to the selected sterilization temperature and maintaining the antiseptic solution in the plurality of containers at the sterilization temperature for the selected sterilization time by contacting, for the duration of the sterilization time, the plurality of containers with a cascading waterfall produced by a cascading water sterilizer;
terminating the heating of the antiseptic solution in the plurality of containers when the selected sterilization time expires; and
cooling the water of the cascading water sterilizer with cooling water produced from a chiller,
wherein after terminating the heating, the antiseptic solution in the plurality of containers has a post-sterilization purity, and
wherein the sterilization temperature and the sterilization time are selected such that after terminating the heating, the antiseptic solution in the plurality of containers is sterile and has a post-sterilization purity of at least about 92% and a percentage point change in purity from the initial purity to the post-sterilization purity of at most about 5%
providing a cascading water sterilizer that produces a cascading waterfall.

28. A method for sterilizing antiseptic solution, the method comprising:
providing a plurality of containers containing the antiseptic solution, the antiseptic solution having an initial purity;
selecting a sterilization temperature from about 85° C. to about 135° C. and a sterilization time from about 1 minute to about 19 hours;
heating the antiseptic solution in the plurality of containers to the selected sterilization temperature and maintaining the antiseptic solution in the plurality of containers at the sterilization temperature for the selected sterilization time by contacting, for the duration of the sterilization time, the plurality of containers with a cascading waterfall produced by a cascading water sterilizer;
heating the water of the cascading waterfall sterilizer with steam produced from one or more boilers; and
terminating the heating of the antiseptic solution in the plurality of containers when the selected sterilization time expires;
wherein after terminating the heating, the antiseptic solution in the plurality of containers has a post-sterilization purity, and
wherein the sterilization temperature and the sterilization time are selected such that after terminating the heating, the antiseptic solution in the plurality of containers is sterile and has a post-sterilization purity of at least about 92% and a percentage point change in purity from the initial purity to the post-sterilization purity of at most about 5% providing a cascading water sterilizer that produces a cascading waterfall.

29. A method for sterilizing antiseptic solution, the method comprising:

provi­ding a plurality of containers containing the antiseptic solution, the antiseptic solution having an initial purity;

selecting a sterilization temperature from about 85° C. to about 135° C. and a sterilization time from about 1 minute to about 19 hours;

heating the antiseptic solution in the plurality of containers to the selected sterilization temperature and maintaining the antiseptic solution in the plurality of containers at the sterilization temperature for the selected sterilization time by contacting, for the duration of the sterilization time, the plurality of containers with a cascading waterfall produced by a cascading water sterilizer;

measuring a change in conductivity of the water of the cascading water sterilizer and correlating the measured change in conductivity to an amount of antiseptic solution present in the water; and terminating the heating of the antiseptic solution in the plurality of containers when the selected sterilization time expires, wherein after terminating the heating, the antiseptic solution in the plurality of containers has a post-sterilization purity, and wherein the sterilization temperature and the sterilization time are selected such that after terminating the heating, the antiseptic solution in the plurality of containers is sterile and has a post-sterilization purity of at least about 92% and a percentage point change in purity from the initial purity to the post-sterilization purity of at most about 5% providing a cascading water sterilizer that produces a cascading waterfall.

* * * * *